United States Patent
Ioudina

(10) Patent No.: US 9,155,766 B2
(45) Date of Patent: Oct. 13, 2015

(54) PROBIOTIC COMPOSITION

(71) Applicant: Integra Medical Inc., London (CA)

(72) Inventor: Natalya Ioudina, London (CA)

(73) Assignee: Integra Medical Inc., London (CA)

( * ) Notice: Subject to any disclaimer, the term of this patent is extended or adjusted under 35 U.S.C. 154(b) by 0 days.

(21) Appl. No.: 13/947,891

(22) Filed: Jul. 22, 2013

(65) Prior Publication Data

US 2014/0023620 A1    Jan. 23, 2014

Related U.S. Application Data

(60) Provisional application No. 61/674,390, filed on Jul. 22, 2012.

(51) Int. Cl.
| | |
|---|---|
| *A01N 63/00* | (2006.01) |
| *A61K 35/744* | (2015.01) |
| *A61K 35/747* | (2015.01) |
| *A61K 31/7016* | (2006.01) |
| *A61K 31/733* | (2006.01) |

(52) U.S. Cl.
CPC ........... *A61K 35/744* (2013.01); *A61K 31/7016* (2013.01); *A61K 31/733* (2013.01); *A61K 35/747* (2013.01)

(58) Field of Classification Search
None
See application file for complete search history.

(56) References Cited

U.S. PATENT DOCUMENTS

| | | | |
|---|---|---|---|
| 6,773,912 B1 * | 8/2004 | Tagg et al. | 435/253.4 |
| 2011/0171283 A1 * | 7/2011 | Riesinger | 424/445 |

FOREIGN PATENT DOCUMENTS

WO    2010077795    7/2010

OTHER PUBLICATIONS

Swanson Ultra Oral Probiotic Formula Strawberry Flavor. Swanson Health Products website. http://www.swansonvitamins.com/SWU519/ItemDetail. Internet Archive Wayback Machine screen capture on May 4, 2011. Accessed on Jul. 9, 2011.*
*Streptococcus salivarius* product sheet. ATCC 2013, pp. 1-2.*
*Lactobacillus paracasei* Lpc-37, Technical Memorandum. Danisco 2008, pp. 1-5.*
Product information for Swanson Ultra oral probiotic, Jul. 23, 2011, https://web.archive.org/web/20110723221333/http://www.swansonvitamins.com/SWU519/ItemDetail, retrieved May 6, 2014.
Marketing materials for Blis BioRestore, Mar. 31, 2008, downloadable from http://web.archive.org/web/20080331100116/http://www.blis.co.nz/prod_biorest_whatis.html, retrieved Mar. 12, 2014.
Thomas, John G., Prebiotics, Probiotics, and Oral Microbial Wellness, Compendium of Continuing Education in Dentistry, vol. 32, Special Issue 3, Oct. 2011.
Reddy, R. Sudhakar, et al., Bacteria in Oral Health—Probiotics and Prebiotics A Review, International Journal of Biological and Medical Research, vol. 2, No. 4, pp. 1226-1233, 2011.

* cited by examiner

*Primary Examiner* — Allison Fox
*Assistant Examiner* — Michelle F Paguio Frising
(74) *Attorney, Agent, or Firm* — Brunet & Co.; Robert Brunet

(57) ABSTRACT

Disclosed herein are probiotic compositions comprising a mixture of at least two probiotic bacteria, including *Streptococcus salivarius* K12® (BLIS K12®) and at least a *Lactobacillus* bacteria. The *Streptococcus salivarius* K12® (BLIS K12®) may comprise *Streptococcus salivarius* K12® (BLIS K12®) BAA1024. The *Lactobacillus* bacteria may be selected from those known to be suitable for oral administration, for example from those known to improve recipient health, particularly recipient oral health.

17 Claims, 2 Drawing Sheets

|  | Ave (mm) | p | SQ |
|---|---|---|---|
| *Alloiococcus otis* 28588T | 31.3 | <0.01 | 1.50 |
| *Corynebacterium diptheriae* 37874T | 3.8 |  | 1.05 |
| *Moraxella catarrhalis* 353T | 10.2 |  | 0.91 |
| *Streptococcus pneumoniae* 28588T | 26.7 |  | 0.94 |

Fig 1.

PROBIOTIC COMPOSITION

CROSS-REFERENCE TO RELATED APPLICATIONS

This application claims the benefit of U.S. Provisional Patent Application No. 61/674,390, filed on Jul. 22, 2012, which is incorporated herein by reference.

FIELD OF THE INVENTION

The present invention relates to probiotic and synbiotic compositions for oral administration. In particular, the present invention relates to probiotic and synbiotic compositions with beneficial effects, such as improved health, especially oral health, and methods of administration of the compositions.

BACKGROUND

The oral cavity shelters numerous and varied microbial flora. When the equilibrium is compromised and when an imbalance appears amongst the indigenous bacteria, pathologies such as dental caries or periodontitis can occur. The beneficial effects of probiotic therapy are achieved in part through the modulation of existing microbial flora associated with the host, thus attaining a balanced and healthy microbes-host relationship.

*S. salivarius* BLIS K12 is a natural human commensal that was isolated from the oral cavity of a healthy New Zealand child. *S. salivarius* is a naturally occurring bacterium, a predominant inhabitant of the back of the tongue and the throat area of humans. *S. salivarius* becomes established in the human oral cavity within two days after birth. The levels of *S. salivarius* in swab samples taken from newborn infants represent 10% of the total streptococci isolated, increasing to 25-30% by one month of age. *S. salivarius* produces two antimicrobial bacteriocins that have been shown to inhibit the growth of oral pathogens.

Probiotic compositions can be enhanced in certain circumstances through the addition of prebiotics to the composition. A prebiotic "feeds" microbial flora; a probiotic adds beneficial cultures to populations of microbial flora. The term "synbiotic" describes a composition that contains both prebiotics and probiotics, for example, one that contains both fructooligosaccharides (FOS) (a prebiotic) and bifidobacteria (a probiotic). Research in the area is devoted to the synergy between the types of ingredients to obtain a better understanding of how growth and survival of probiotics may be enhanced by the presence of complementary prebiotic ingredients. There is no guarantee that a prebiotic will enhance the efficacy of a probiotic composition in all cases, nor of the relative amounts of prebiotics required relative to probiotics to achieve a beneficial effect in a particular composition.

Although a large number of probiotic compositions are known, each composition has unique characteristics and particular health benefits. However, there is always a need for improved formulations of probiotic compositions, particularly formulations that result in one or more of improved oral health, improved oral bioavailability, improved shelf-life, decreased incidence of side effects, and additional improvements, as well as methods of administration or uses thereof.

SUMMARY OF THE INVENTION

In one aspect, there is provided a probiotic composition comprising a mixture of at least two probiotic bacteria, including *Streptococcus salivarius* K12® (BLIS K12®) and at least a *Lactobacillus* bacteria.

In another aspect, there is provided a probiotic composition comprising a mixture of at least six probiotic bacteria, including *Streptococcus salivarius* K12® (BLIS K12®) and at least five *Lactobacillus* bacteria.

In yet another aspect, there is provided a method of improving oral health, comprising administering a probiotic composition comprising a mixture of at least six probiotic bacteria, including *Streptococcus salivarius* K12® (BLIS K12®) and at least five *Lactobacillus* bacteria to a recipient twice a day for a sequential period of days sufficient to produce a measurable improvement in at least one oral health parameter.

Further embodiments of the invention will be described with reference to the following detailed description.

BRIEF DESCRIPTION OF THE DRAWINGS

Having summarized the invention, embodiments thereof will now be described with reference to the accompanying figures in which:

FIG. 1 shows synergistic antagonism for the combination of *Streptococcus salivarius* K12® (BLIS K12®) and *L. plantarum* Lpc37 strains against various ear nose and throat (ENT) pathogenic organisms (comparison was made to component strains individually by one-way ANOVA with data from 6 individually repeated experiments);

DETAILED DESCRIPTION

Figure 2:
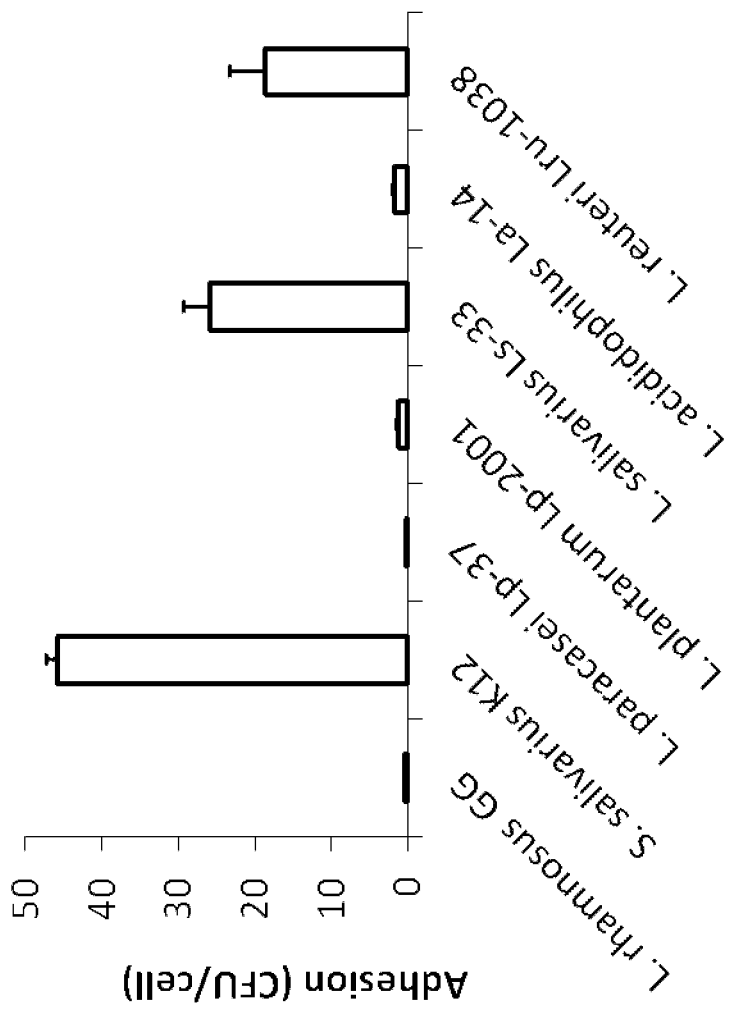
FIG. 2 shows adhesion of a combination of probiotic strains to human bronchial epithelial cell line 16HBE14o-.

Disclosed herein are probiotic compositions comprising a mixture of at least two probiotic bacteria, including *Streptococcus salivarius* K12® (BLIS K12®) and at least a *Lactobacillus* bacteria. The *Streptococcus salivarius* K12® (BLIS K12®) may comprise *Streptococcus salivarius* K12® (BLIS K12®) BAA1024. The *Lactobacillus* bacteria may be selected from those known to be suitable for oral administration, for example from those known to improve recipient health, particularly recipient oral health.

The *Lactobacillus* bacteria may comprise *Lactobacillus paracasei* and/or *Lactobacillus plantarum*, for example *Lactobacillus paracasei* Lpc-37 SD5275 and/or *Lactobacillus plantarum* Lp-2001 SD5870.

Alternatively or additionally to *Lactobacillus paracasei* and/or *Lactobacillus plantarum*, the *Lactobacillus* bacteria may comprise *Lactobacillus reuteri*, for example *Lactobacillus reuteri* Lru-1038 SD5865.

The probiotic composition may further comprise *Lactobacillus salivarius* and/or *Lactobacillus acidophilus*, for example *Lactobacillus salivarius* Ls-33 SD5208 and/or *Lactobacillus acidophilus* La-14 SD5212.

In one embodiment, the composition may comprise *Streptococcus salivarius* K12® (BLIS K12®), *Lactobacillus paracasei*, *Lactobacillus plantarum*, *Lactobacillus reuteri*, *Lactobacillus salivarius* and *Lactobacillus acidophilus*. These may be provided in amounts of 25%, 25%, 15%, 10%, 15% and 10%, respectively, based on the total amount of colony forming units (CFU) in the composition. An exemplary form of this embodiment is provided in Table 1.

TABLE 1

Probiotic Composition

| Active Ingredients | Amount/Tablet | |
|---|---|---|
| | (% based on 1 Billion CFU/tablet) | (mg) |
| S. salivarius K12 ®(BLIS K12 ®) BAA1024 | 25% (~2.5 × 10⁸ CFU) | 6* |
| Mixture of 5 Probiotic Lactobacteria: | | 126 |
| Lactobacillus paracasei Lpc-37 SD5275 | 25% (~2.5 × 10⁸ CFU) | |
| Lactobacillus plantarum Lp-2001 SD5870 | 15% (~1.5 × 10⁸ CFU) | |
| Lactobacillus salivarius Ls-33 SD5208 | 15% (~1.5 × 10⁸ CFU) | |
| Lactobacillus acidophilus La-14 SD5212 | 10% (~1.0 × 10⁸ CFU) | |
| Lactobacillus reuteri Lru-1038 SD5865 | 10% (~1.0 × 10⁸ CFU) | |

*6 mg input = 25% of mixture, based on manufacturing loss data

The target CFU count per tablet is 1 Billion (1.0×10⁹ CFU) upon manufacturing, with total minimum CFU per tablet of 1×10⁸ CFU at the end of 18 months at room temperature. It should be noted that the total number of colony forming units (CFU) per tablet may vary in a range of from 80 to 300% of the nominal value listed in Table 1.

In one embodiment, the relative amounts of the top three ingredients may be increased individually or in combination by an amount of from 0.1 to 50% of the amount listed in Table 1, with the balance being taken from the remaining ingredients. In another embodiment, the relative amount of the fourth ingredient may be increased in an amount of from 0.1% to 300%, with the balance being taken from the remaining *Lactobacillus* bacteria.

In cases of conflict between the weight and percentage values listed in Table 1 (for example, in the event that a higher dose formulation is provided), the percentage values of the active ingredients take priority in order to preserve the same relative number of CFU of each ingredient in the composition.

Although a variety of substitutions of the ingredients listed in Table 1 may be made according to the previous description, particular potential substitutions are listed in Table 2.

TABLE 2

Permissible substitutions

| Original Probiotic strains in Table 1 | Potential substitutions |
|---|---|
| 1) S. salivarius K12 ® (BLIS K12 ®) BAA1024 | S. salivarius BLIS M18 ® |
| 2) Lactobacillus paracasei Lpc-37 SD5275 | L. paracasei Lpc-9007 SD5850 |
| 3) Lactobacillus plantarum Lp-2001 SD5870 | |
| 4) Lactobacillus salivarius Ls-33 SD5208 | Ls-9010 SD5863 |
| 5) Lactobacillus acidophilus La-14 SD5212 | La-9004 SD5864 |
| 6) Lactobacillus reuteri Lru-1038 SD5865 | |

In another embodiment, the composition comprises the active ingredients as described above in combination with one or more prebiotic ingredients. Such a composition may be referred to as a synbiotic composition. The prebiotic ingredients may comprise lactitol, inulin, or a combination thereof. The lactitol may be provided in an amount of from 1 to 50% by weight of the composition. The inulin may be provided in an amount of from 1 to 25% by weight of the composition. These prebiotic ingredients may be provided in conjunction with a number of other excipients suitable for oral administration. Relative amounts of exemplary prebiotic ingredients and other excipients are provided in Table 3.

TABLE 3

Prebiotic Ingredients and Excipients

| Ingredients and Excipients | Amount/tablet (mg) |
|---|---|
| Lactitol | 180 |
| Inulin | 65 |
| Dicalcium Phosphate | 50 |
| Blueberry Flavor (natural) | 20 |
| Dextrose | 15 |
| Fructose | 15 |
| Stearic Acid | 10 |
| Citric Acid | 6 |
| *Vanilla* Flavor (natural) | 1.25 |
| Stevia Rebaudioside A (97%) | 0.3 |

A particularly notable synbiotic composition comprises the active ingredients listed in Table 1 along with the prebiotic ingredients and other excipients listed in Table 3. The nominal estimated gross weight of a tablet according to this preferred embodiment is 494.55 mg (~495 mg). This amount may vary from tablet to tablet by from 0 to +10%.

The shelf life of the composition may be from 18-24 months at room temperature (15-30° C., or ~25° C.) and from 24-36 months at refrigeration temperatures (2-8° C., or ~4° C.). In order to improve shelf life and other viability parameters, the composition may be manufactured using the Live-Bac® process, which is described in U.S. Pat. Nos. 6,627,220 and 7,150,623 to Nutraceutix, Inc. (Redmond, Wash.) both of which are incorporated herein by reference.

The composition is formulated for oral administration. Oral administration may be achieved using a chewable formulation, a dissolving formulation, an encapsulated/coated formulation, a multi-layered lozenge (to separate active ingredients and/or active ingredients and excipients), a slow release/timed release formulation, or other suitable formulations known to persons skilled in the art. Although the word "tablet" is used herein, the formulation may take a variety of physical forms that may commonly be referred to by other terms, such as lozenge, pill, capsule, or the like. For administration to children, the product may be flavoured (e.g. fruit flavored, such as blueberry) and may be in a variety of shapes that are pleasing to children (stars, animals, popular characters, smiley faces, etc.). The product may be formulated as part of a gummy candy in order to improve acceptance by children.

A method of administration or use of the composition for improving oral health comprises oral administration of the composition by chewing twice daily for a sequential period of days sufficient to produce a measurable improvement in at least one oral health parameter.

The composition may provide a number of benefits, especially health benefits. The composition may provide improved oral bioavailability, improved shelf-life, decreased incidence of side effects, etc. The composition may improve recipient health, particularly oral health. Improvements in oral health may include a reduction in the incidence, amount or severity of dental caries, gingivitis, halitosis, ENT infection, or other relevant oral health parameter. Improvements in oral health may particularly be manifested in pediatric populations.

EXAMPLES

Example 1

Probiotic Compositions Synergistically Inhibit ENT Pathogens

Ear, nose, and throat (ENT) infections are very common diseases that specifically affect the ears, the sinuses, and the upper respiratory tract. There are numerous bacteria that are responsible for these infections some of the most common ones being *Streptococcus pneumoniae, Haemophilus influenzae* and *Moraxella catarrhalis*. The manifestation of disease can range from a mild cold to a severe pharyngitis. The ENT cavities are connected by the pharynx. The Eustachian tube connects the middle ear to the nasopharynx. Ear infections or Otitis media, are very common ENT problems, especially in children. Otitis media, or "otitis" is named after the well known pathogen *Alloiococcus otis*, which is the pathogen most commonly found in children with otitis media with effusion (Hendolin, 1999). *A. otis* overgrowth in the middle ear, often caused by fluid blockage of the Eustachian tube leads to infection, and potential long term damage. Otitis media is the most common cause of pediatric visits as well as antibiotic administration during the first years of life.

To determine the synergistic effects of probiotic compositions as described herein against ENT pathogens, antagonism screening was undertaken with individual component strains of the probiotic composition as well as combinations. The ENT pathogens assayed were *Alloiococcus otis, Corynebacterium diptheriae, Moraxella catarrhalis*, and *Streptococcus pneumoniae*. Deferred antagonism assays against these four ENT pathogens allowed the quantification of the relative antimicrobial characteristics of the individual strains, and also in combination.

The assay was undertaken essentially as previously performed by Tagg and Bannister (Tagg 1979). Liquid cultures were inoculated into MRS for lactobacilli, BHYE for streptococci, and soy-tripticase with 20% sheep's blood for ENT pathogens (37° C., microaerophilic). Overnight suspensions of probiotics were swabbed onto Columbia blood plates (44 g/L, Difco) supplemented with defibrinated sheep's blood (5% v/v, Cedarlane) in a measured 1 cm wide streak using sterile cotton swabs. After 48 hours (37° C., microaerophilic), bacterial growth was removed from the surface and the plate re-sterilized with chloroform vapors for 20 minutes. Overnight suspensions of the ENT pathogen type-strains *Alloiococcus otis* 28588T, *Corynebacterium diptheriae* 37874T, *Moraxella catarrhalis* 353T, and *Streptococcus pneumoniae* 28588T were then streaked across perpendicularly, and the plates were re-incubated (37° C., microaerophilic, 48 hrs). The zone of inhibition (ZOI) was calculated as the distance between the two areas of bacterial growth, minus 1 cm. One way-ANOVAs were used to compare between specific probiotics and probiotic combinations. Synergism was calculated as a synergistic quotient (SQ), which is the sum of the individual treatments divided by the combined treatment. Values >1 indicate synergism of the combination (Wang 2012).

FIG. 1 indicates the zone of inhibition (ZOI) that was calculated when combining *Streptococcus salivarius* K12, and *Lactobacillus paracasei* Lpc-37. It was found that there was significant antagonism. When averaged across 6 experiments and compared to the individual strains *S salivarius* K12, and *L. paracasei* Lpc-37 on their own, their combination was shown to be synergistic in antagonizing *Alloiococcus otis* 28588T. The combination yielded a 50% greater effect than either component strain individually.

Example 2

Adhesion to Human Cells

It is advantageous that probiotic compositions co-localize with the ENT pathogens within the oral cavity to better deliver inhibitory effects. To test the potential of the probiotic bacteria to stay within the oral cavity, binding affinity assays were performed.

The immortalized human bronchial epithelial cell line 16HBE14o- was grown using standard cell culture procedures at 37° C. and 5% $CO_2$ (MEM, 10% FBS and 2 mM L-glutamine). Cells were seeded at $1 \times 10^5$ cells/well in tissue-culture treated 24-well plates, and grown to confluency. Media was then replaced with media containing 100-fold dilutions of bacterial cell suspensions. After 5 hours incubation, the monolayers washed thoroughly three times with PBS to remove non- or loosely-adherent bacteria. Eukaryotic cells were then disrupted by adding Triton™ X-100 (0.1%). The remaining adherent bacteria contained in the lysis suspension were enumerated by drop plate method. Adhesion was reported as total CFUs divided by the number of bronchial cells in the well as determined by cell counts of a bacteria-free control well of 16HBE14o- cells. The results of these assays are reported in FIG. 2.

The assay tested adherence of the bacteria to a monolayer of 16HBE14o- human bronchial epithelial cells, which share a cell linage with oral epithelial cells and resemble them in phenotype. It was found that *S. salivarius* K12, *L. salivarius* Ls-33 and *L. reuteri* Lru-1038 where able to strongly adhere to the oral cavity analogue, providing an expectation that the inhibitory effects observed in vitro would likely manifest themselves clinically.

The invention has been described in detail solely for purposes of illustration, and it is understood that variations and sub-combinations of the invention as described can be conceived by those skilled in the art. Such variations and sub-combinations are intended by the inventor to be covered within the scope of the claims. Therefore, the invention is limited solely by the terms of the claims provided hereinafter and the claims are intended to be construed broadly by persons of skill in the art.

The invention claimed is:

1. A probiotic composition comprising a synergistic mixture of at least two oral health improving probiotic bacteria, including *Streptococcus salivarius* K12® (BLIS K12®) and *Lactobacillus paracasei* Lpc-37 SD5275, formulated for oral administration.

2. The composition of claim 1, wherein the *Streptococcus salivarius* K12® (BLIS K12®) comprises *Streptococcus salivarius* K12® (BLIS K12®) BAA1024.

3. The composition of claim 1, further comprising *Lactobacillus plantarum*.

4. The composition of claim 3, wherein the *Lactobacillus plantarum* comprises *Lactobacillus plantarum* Lp-2001 SD5870.

5. The composition of claim 3, further comprising *Lactobacillus reuteri*.

6. The composition of claim 5, wherein the *Lactobacillus reuteri* comprises *Lactobacillus reuteri* Lru-1038 SD5865.

7. The composition of claim 5, further comprising *Lactobacillus salivarius* and *Lactobacillus acidophilus*.

8. The composition of claim 7, wherein the *Streptococcus salivarius* K12® (BLIS K12®) is provided in an amount of 25% of the colony forming units (CFU) of the composition, the *Lactobacillus paracasei* is provided in an amount of 25% of the colony forming units (CFU) of the composition, the *Lactobacillus plantarum* is provided in an amount of 15% of the colony forming units (CFU) of the composition, the *Lactobacillus reuteri* is provided in an amount of 10% of the colony forming units (CFU) of the composition, the *Lactobacillus salivarius* is provided in an amount of 15% of the colony forming units (CFU) of the composition, and the *Lac-* tobacillus acidophilus is provided in an amount of 10% of the colony forming units (CFU) of the composition.

9. The composition according to claim 7, comprising lactitol and inulin.

10. The composition according to claim 9, wherein the lactitol is provided in an amount of from 1 to 50% by weight of the composition and the inulin is provided in an amount of from 1 to 25% by weight of the composition.

11. The composition of claim 1, further comprising *Lactobacillus reuteri*.

12. The composition of claim 11, wherein the *Lactobacillus reuteri* comprises *Lactobacillus reuteri* Lru-1038 SD5865.

13. The composition of claim 1, further comprising *Lactobacillus salivarius* and/or *Lactobacillus acidophilus*.

14. The composition of claim 13, further comprising *Lactobacillus salivarius* Ls-33 SD5208 and/or *Lactobacillus acidophilus* La-14 SD5212.

15. The composition according to claim 1, comprising one or more prebiotic ingredients.

16. The composition according to claim 15, comprising lactitol, inulin, or a combination thereof.

17. The composition of claim 1, wherein administration of the composition to a recipient improves oral health of the recipient.

* * * * *